United States Patent

Gabriel

[11] Patent Number: 5,149,624
[45] Date of Patent: Sep. 22, 1992

[54] METHOD FOR DETECTING BACTERIAL OR FUNGAL DISEASES IN PLANTS

[75] Inventor: Dean W. Gabriel, Gainesville, Fla.

[73] Assignee: University of Florida, Gainesville, Fla.

[21] Appl. No.: 916,102

[22] Filed: Oct. 7, 1986

[51] Int. Cl.⁵ ............................................. C12Q 1/68
[52] U.S. Cl. .................................... 435/6; 435/179;
 436/501; 436/530; 436/178; 436/804; 436/56;
 935/78
[58] Field of Search ............................ 435/6, 35, 179;
 436/501, 530, 56, 178, 804; 935/78

[56] References Cited

U.S. PATENT DOCUMENTS 4,358,535 11/1982 Falkow et al. ..................... 435/35

OTHER PUBLICATIONS

Rosner et al, J. Gen. Virol. (1983), 64, 1757-1763.
Maule et al, J. Virol. Methods (1983), 6, 215-224.

Primary Examiner—Amelia Burgess Yarbrough
Attorney, Agent, or Firm—Kerkam, Stowell, Kondracki & Clarke

[57] ABSTRACT

Complementary DNA probe method for diagnosing bacterial or fungal diseases which produce leaf lesions in plants.

10 Claims, 1 Drawing Sheet

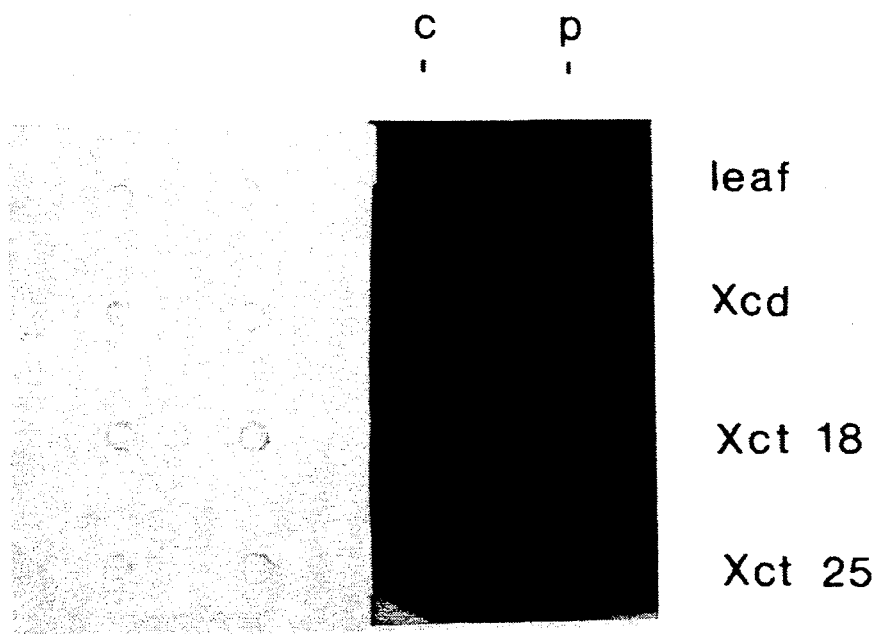
FIG. I

METHOD FOR DETECTING BACTERIAL OR FUNGAL DISEASES IN PLANTS

BACKGROUND OF INVENTION

1. Field of the Invention

The present invention relates to methods for diagnosing plant diseases.

2. Prior Art

The classical and accepted methods for diagnosing bacterial and fungal diseases in plants involves isolating the microbe in pure culture from a diseased plant, inoculating test plants, and reisolating the microbe from the test plant after observing the same disease symptoms of those originally found. This procedure is tedious, time-consuming and requires a high level of experience with the plant and with the suspected microorganisms. Moreover, the microbes; because of their plant pathogenic growth preferences, very often grow slowly or not at all in pure culture.

The reliable diagnosis of plant diseases, therefore, requires sophisticated laboratories, equipment and highly-trained personnel. In practice and in the field, amateur and small-scale agricultural growers do not have ready access to the experienced personnel and/or laboratories necessary for these diagnoses. The time, effort and costs involved are not justified by the limited utility of the information to the small-scale grower. Even on a large-scale, decisions as to frequently costly intervention measures must be made quickly in order to save the plants infected by the suspected diseases. The time frame required for a confirmed diagnosis according to the classical method is unduly lengthy. Therefore, expediency requires that such decisions be made on the basis of prior experience with the disease and the specific infected plant type. These decisions may prove to be erroneous in the worst cases, thereby resulting in the loss of valuable plants and/or the utilization of improper methods of treatment.

It has been proposed to utilize "recombinant DNA(rDNA) probes" containing cloned fragments of DNA specific for selected viral microbes to identify viral diseases in plants. See U.S. Pat. No. 4,480,040; Gould et al, Journal of Virological Methods, Vol. 2, pp. 287–292 (1981); Eden et al, Journal of Bacteriology, August 1974, pp. 547–553; Allen et al, Ann. Appl. Biol., Vol. 98, pp. 451–461 (1981); Palukaitis et al, Ann. Appl. Biol., Vol. 98, pp. 439–449 (1981).

The procedure described in U.S. Pat. No. 4,480,040 is typical of the prior art DNA probe techniques for diagnosing viral and viroid diseases in plants. Generally, these techniques require a time-consuming and expensive preparation of a purified or partially purified plant extract to conduct the diagnosis. The need for an extraction or partial purification step in order to successfully detect diseases in plants necessarily lengthens the time required and increases the cost for successfully diagnosing plant viral diseases.

The distinctions between bacterial and fungal diseases on the one hand and viral diseases on the other is well known to those skilled in the art. The detection of viruses and viroids normally requires the use of biochemical diagnostic techniques such as serology, protein electrophoresis and/or DNA hybridizations. The diagnosis of bacterial and fungal diseases is relatively simpler in that they are readily identifiable by simple microbial tests after culturing. Viral diseases are not amenable to this type of diagnosis because they cannot be cultured, and the more sophisticated laboratory tests are necessary. However, even classical methods of diagnosing bacterial and fungal diseases are expensive, lengthy and time-consuming as noted above.

The application of DNA hybridization technology to plant disease detection and diagnosis was developed by necessity as the only rapid means available for the detection of viroids in plants [Owens, et al (1981), Science 213:670–672]. Since viroids consist of replicating, unencapsulated RNA, direct hybridization of complementary DNA (cDNA) probes to plant cell-sap concentrates was a workable idea. Since unencapsulated RNA or DNA is an important stage of the life cycle of viruses, the same technique could be directly applied to viral plant pathogens. However, since bacterial and fungal DNA is contained within the protective cell walls of these organisms (as opposed to viruses and viroids), the DNA thereof is obviously not available for hybridization without removal from within the cells using an extraction procedure.

Although in situ lysis and hybridization procedures have been developed for bacteria and fungi [Grunstein et al (1975), Proc. Natl. Acad. Sci., USA 72:3961–3965, and Stohl et al (1983), Anal. Biochem. 134:82–85], all such techniques rely upon macroscopically visible bacterial or fungal colonies grown on culture media. Bacterial and fungal disease organisms which produce leaf lesions in plants are generally not known to achieve sufficiently high population levels within the leaf to allow ready detection with current DNA probe technology. Those skilled in the art would conclude that it would first be necessary to culture the microbes outside of the leaf to achieve a sufficiently high population for detection.

It has been proposed to use rDNA probes to detect bacterial pathogens of human in excreta or physiological fluid, without extraction or purification [U.S. Pat. No. 4,358,535, Dallas et al (1979). Proceedings of the 13th Joint Conference on Cholera, U.S. Department of Health, Education and Welfare publication No. NIH 78-1590, p. 71–80, NIH, Bethesda, Md., and Dallas et al (1979), in K. N. Timmis and A. Puhler (ed.), Plasmids of medical, environmental, and commercial importance, Elsevier/North Holland Publishing Co., Amsterdam, p. 113–122].

It is an object of the present invention to provide a rDNA probe technique for detecting or diagnosing bacterial and fungal diseases in plants which produce leaf lesions, said procedure being efficient and inexpensive and capable of being effectuated by relatively untrained personnel and without the requirement for sophisticated equipment. The invention is unique in that no partial purification, concentration or extraction procedure or apparatus designed for these purposes need be employed.

SUMMARY OF THE INVENTION

The foregoing and other objects are produced by the present invention which contemplates a method for detecting and identifying bacterial or fungal diseases in plants, the disease being one which produces leaf lesions in the plant, comprising:

(a) providing a sample of pathogen cells from the leaf lesions in the plant, (b) binding the pathogen cells to a solid support, (c) disrupting the pathogen cells bound to the support whereby the DNA of the cells is released therefrom and becomes bound to the support, (d) probing the DNA bound to the support with an assayable DNA that is complementary to the bacterial or fungal RNA to be detected whereby any bacterial- or fungal-RNA or bacterial- or fungal- DNA is hybridized to form an assayable DNA-bacterial or -fungal RNA hybrid or an assayable DNA-bacterial or -fungal DNA hybrid, and (e) subjecting the probed material to an assay to detect the presence of any of the hybrids.

BRIEF DESCRIPTION OF THE DRAWING

FIG. 1 is a developed x-ray film for a typical leaf squash hybridization according to the present invention.

DETAILED DESCRIPTION OF THE INVENTION

The method of the invention is applicable for the detection of any bacterial or fungal organism which produces leaf lesions in plants, e.g., all *Xanthomonas campestris* pathovars (for listing of those described to date, see Krieg, N. R., and J. G. Holt (1984), Bergey's Manual of Systematic Bacteriology, Vol. 1, Williams and Wilkins, Baltimore, pp. 204–209), *Pseudomonas syringae* pathovars, *Erwinia stewartii*, *Erwinia rubrifaciens*, *Clavibacter michiganense* and subspecies, *Clavibacter xyli* and subspecies, *Phytopthora infestans*, Valsa spp., Nectria spp., Mycosphaerella spp., Venturia spp., Coccomyces spp., Leptospaherulina spp., Pseudopeziza spp., Rhytisma spp. Sclerotina sp., Alternaria spp., Stemphylium spp., Phomopsis sp., Phoma spp., Phyllosticta sp., Colletotrichum, sp., Cercospora sp., Helminthosporium sp., Septoria sp., Rhynchosporium sp., and Typhula sp. The above list is not meant to be inclusive, as all plants affected by foliar spotting diseases are amenable to the method of the invention. The specific example used to illustrate the invention is *Xanthomonas campestris* pv. citri, cause of citrus canker disease.

Plants affected by foliar spotting diseases are amenable to the method of the invention.

The method of the invention is particularly applicable for detecting *Xamthomonas campestris* pv. citri (Xct), the causal agent of citrus canker. The rapid and accurate diagnosis of citrus canker is highly important from an economic standpoint. For example, eradication efforts in Florida have presently affected at least ten percent of the state's citrus nurseries. Rapid diagnosis is essential in that citrus canker is world-wide in distribution and that decisions on roguing and the timing of bactericidal sprays and treatments must be made rapidly. The bacterial organism which causes citrus canker is typical of many other leaf-inhabiting microbes and the method of the present invention can be applied in a similar manner to a wide variety of other such leaf lesion producing pathogenic organisms.

The method of the invention is relatively simple, efficient and rapid in that all that is required is the squashing or crushing of a portion of the leaf lesion onto a suitable solid support such as a filter paper or other cellulosic material, etc., and insuring that at least a portion of the cells in the lesion are disrupted, i.e., crushed or lysed so as to release the DNA therein followed by probing of the released DNA with an assayable DNA complementary to the bacterial or fungal RNA to be detected thereby hybridizing the former.

The assayable DNA may be colorimetrically or radiographically assayable.

The DNA probe or probe mixture appropriate for the target organism is selected and nick-translated with a biotinylated nucleotide prior to the field work. Nick-translation of the probe is accomplished according to directions supplied with commercially available biotinylation kits. The probe may be stored for several months in a standard freezer ($-20°$ C.). Squashed, denatured and neutralized samples on filters may be stored for over a year or immediately hybridized as follows: the filter is wetted with 6X SSC (1X SSC is 0.15M NaCl and 0.015M Na$_3$Citrate) for 5 minutes and pre-hybridized in a sealable bag containing 5 ml of hybridization solution (0.25% non-fat dry milk and 6X SSC) for 1 hr. at 65° C. The probe is denatured in a boiling water bath for 10 minutes, and then added to the bag with a filter and incubated at 65° C. for 3–16 hrs. The filter is removed and rinsed at room temperature for 5 minutes in 125 ml of 2X SSC and 0.1% sodium dodecyl sulfate (SDS), and then for 15 minutes in 0.2% SSC and 0.1% SDS. The filter is then twice rinsed in 0.2X SSC and 0.1% SDS for a total of one hour. Finally, the filter is blocked, reacted with streptavidin and then biotin as described in the biotinylation protocol. Color development peaks in about four hours, and samples are photographed and/or visually scored at this time.

Generally, the mere squashing or crushing of the leaf lesion onto the support material and subsequent alkaline lysis is sufficient to release the DNA from the bacterial cells. On occasion, however, it may be necessary to subject the transferred lesion material to enzymatic lysis to release the DNA, from the cells. Suitable enzymes for bacterial lysis include lysozyme and proteinase K. Suitable enzymes for fungal cell lysis include lyticase, zymolyase, glusulase or Novozym, according to protocols similar to that described by Stohl et al (op. cit.).

The alkaline lysis step is perhaps the most critical step in the procedure, since a number of biologically significant events occur simultaneously which are not obvious. Unless the DNA degrading enzymes present in the crushed leaf sample and in the dying pathogen cells are inactivated, DNA or RNA from the bacteria or fungi in the sample will be degraded and lost. Many of these enzymes are inactivated by the oxidation of phenolic compounds released by the plant upon wounding during the squash procedure. Further inactivation of these enzymes is accomplished during the alkaline lysis step in the procedure. This also accomplishes sterilization of the sample by lysis, and satisfies USDA-APHIS and state quarantine regulations so that the sample can be shipped for assay. Finally, the DNA in the lysed cells is denatured and fixed to the support material.

The invention is illustrated by the following non-limiting example.

EXAMPLE

The method of the invention generally only requires a piece of ordinary filter paper (Watman 607 is recommended), a blunt instrument (such as a Q-tip), a petri dish, a pre-hybridization solution (where necessary) and 3 hybridization solutions. The three hybridization solutions utilized herein are: A, 0.5M NaOH, 1.5M NaCl; B, 3M NaCL, 0.5M Tris-HCl, pH 7.1–7.5; and C, 0.3M NaCL, 0.03M sodium citrate. When necessary, a prehybridization lysing solution containing lysozyme, proteinase K and/or lyticase may be used.

If a bacterium like Clavibacter is resistant to alkaline denaturation, then prior to hybridization the filters are first soaked in 50 mM Tris, pH 8.5, 50 mM EDTA, 15% sucrose and 1 mg/ml lysozyme for 15 minutes. Proteinase K is added to 0.5 mg/ml, and the incubation continued for 30 minutes at 37° C. If a fungal pathogen is suspected, the filters are incubated for 30 minutes in 10 ml of 1M sorbitol, 0.1M citrate, pH 5.8, 50 mM EDTA, 50 mM dithiothreitol and 100 ul of 100% glusulase or equivalent enzyme.

Small circles of ca. 4 mm diameter are drawn on the filter paper and labeled for each sample to be taken. The blunt end of a Q-tip is used to squash a portion of the lesion to be tested directly onto the filter paper, within the labeled circle. As many samples are taken as can be fit on the filter within a 30 minute time limit. Typically, 50 samples can be fitted easily on a standard 9 cm diameter filter. Before 30 minutes have elapsed since the first sample was taken, the filter is placed in a petri dish with 10 ml of solution A and allowed to soak for 15 minutes. Solution A is then discarded and replaced by 20 ml of solution B; the filter is left to soak for 15 minutes. Solution B is then discarded and replaced by 20 ml of solution C; the filter is left to soak for 5 minutes. Solution C is then discarded and the filter allowed to dry. The filter paper with samples may then be: 1) stored for months; 2) mailed to a lab for analysis; or 3) tested with a field hybridization kit. Processing the filter presently requires ca. 24 hours with a $^{32}P$-labeled probe.

In practice, the detection limit of a $^{32}P$-labeled, rDNA probe of ca. 20 kb size is roughly $5 \times 10^3$ bacteria/4 mm$^2$ spot. (A bacterium contains about 0.0044 pg of DNA; therefore $5 \times 10^3$ bacterial contain ca. 22 pg of DNA.) This limit is achieved on nitrocellulose filters, and agrees well with other published data. On an ordinary piece of filter paper, the detection limit is ca. $2.5 \times 10^4$ bacteria/4 mm$^2$. Populations of citrus canker within citrus leaf lesions normally reach $10^8$ bacteria/cm$^2$ or $4 \times 10^6$/4 mm$^2$. This is well above the detection threshold. Non-pathogenic bacteria have never been reported to achieve levels even approaching this detection threshold.

For autoradiography, the rDNA probe is nick-translated using a $^{32}P$-labeled nucleotide and a commercially available kit and protocol. The nick-translated probe is useful for about a week. The squashed samples are pre-hybridized, hydribidized and rinsed as described for the colorimetric assay. The filter is then dried and placed next to a sheet of X-ray film overnight at $-100°$ C. The X-ray film is developed and kept as a permanent record.

FIG. 1 is a developed x-ray film for a typical leaf squash hybridization. On the left is filter paper with circled areas indicating squashed samples. On the right is an autoradiograph of filter after hybridization with isolate 11 plasmid ('c'=center, 'p'=periphery). Citrus canker (Xet) isolates 18 and 25 are indicated. Controls are pv. diefenbachia (Xed) and uninoculated leaf. All isolates were artificially inoculated.

I claim:

1. A method for detecting a bacterial or fungal disease in a plant, said disease characterized by the presence of leaf lesions containing bacterial or fungal pathogen cells in said plant, comprising:
   a) providing a sample of said pathogen cells free from DNA and RNA degrading enzymes from said leaf lesions,
   b) binding said pathogen cells to a solid support,
   c) disrupting said pathogen cells bound to said support whereby the DNA of said cells is released therefrom and is bound to said support,
   d) probing said DNA bound to said support with an assayable DNA that is complementary to the bacterial or fungal RNA to be detected whereby any bacterial- or fungal-RNA or bacterial- or fungal-DNA is hybridized to form an assayable DNA-bacterial or -fungal RNA hybrid or an assayable DNA-bacterial or -fungal DNA hybrid; and
   e) subjecting the probed material to an assay to detect the presence of any of said hybrids.

2. The method of claim 1 wherein said plant is a citrus plant.

3. The method of claim 1 wherein said plant disease is *Xanthomonas compestris* pv. citri (Xct).

4. The method of claim 1 wherein said pathogen cells are bound by being placed on cellulosic support.

5. The method of claim 4 wherein said cellulosic support is filter paper.

6. The method of claim 1 wherein said pathogen cells are disrupted by crushing and lysing by contact with a lysing agent selected from the group consisting of an enzyme and/or an alkali.

7. The method of claim 1 wherein said assayable DNA is colorimetrically assayable.

8. The method of claim 1 wherein said assayable DNA is radiographically assayable.

9. The method of claim 8 wherein said radiographically assayable DNA is labeled with a radioisotope.

10. The method of claim 9 wherein said radioisotope is $^{32}P$.

* * * * *

UNITED STATES PATENT AND TRADEMARK OFFICE
CERTIFICATE OF CORRECTION

PATENT NO.  : 5,149,624

DATED       : Sept. 22, 1992

INVENTOR(S) : GABRIEL, Dean W.

It is certified that error appears in the above-identified patent and that said Letters Patent is hereby corrected as shown below:

Column 1, following BACKGROUND OF INVENTION, insert the following paragraph:

-- Research leading to the completion and reduction to practice of the invention described in the application was supported, in part, by Grant No. 58-43YK-5-3 issued by the U.S. Department of Agriculture (USDA). The United States Government has certain right to t'e invention claimed herein. --

Signed and Sealed this

Twenty-eighth Day of September, 1993

Attest:

BRUCE LEHMAN

*Attesting Officer*  *Commissioner of Patents and Trademarks*